(12) United States Patent
Schmidtke et al.

(10) Patent No.: US 8,293,075 B2
(45) Date of Patent: *Oct. 23, 2012

(54) METHOD FOR THE CONTINUOUS SEPARATION BY DISTILLATION OF MIXTURES THAT CONTAIN MORPHONLINE (MO), MONOAMINODIGLYCOL (ADG), AMMONIA AND WATER BY MEANS OF DISTILLATION

(75) Inventors: Helmut Schmidtke, Bensheim (DE); Oliver Bußmann, Ludwigshafen (DE); Ralph Versch, Eppelsheim (DE); Udo Rheude, Otterstadt (DE); Uwe Leyk, Worms (DE); Manfred Julius, Limburgerhof (DE); Martin Rudloff, Gönnheim (DE); Erhard Henkes, Einhausen (DE)

(73) Assignee: BASF SE, Ludwigshafen (DE)

( * ) Notice: Subject to any disclaimer, the term of this patent is extended or adjusted under 35 U.S.C. 154(b) by 840 days.
This patent is subject to a terminal disclaimer.

(21) Appl. No.: 12/443,581

(22) PCT Filed: Sep. 12, 2007

(86) PCT No.: PCT/EP2007/059557
§ 371 (c)(1),
(2), (4) Date: Mar. 30, 2009

(87) PCT Pub. No.: WO2008/037590
PCT Pub. Date: Apr. 3, 2008

(65) Prior Publication Data
US 2012/0024689 A1 Feb. 2, 2012

(30) Foreign Application Priority Data

Sep. 28, 2006 (EP) .................................... 06121428

(51) Int. Cl.
*B01D 3/14* (2006.01)
*C07D 295/02* (2006.01)

(52) U.S. Cl. ................. 203/14; 203/29; 203/38; 203/75; 203/77; 203/78; 203/80; 203/98; 203/99; 203/DIG. 19; 544/106; 564/479; 568/868

(58) Field of Classification Search .................... 203/14, 203/29, 38, 75, 77, 78, 80, 98, 99, DIG. 19; 544/106; 564/479, 480; 568/852, 868; 202/4, 202/155, 158
See application file for complete search history.

(56) References Cited

U.S. PATENT DOCUMENTS 3,154,544 A    10/1964   Landon et al.
(Continued)

FOREIGN PATENT DOCUMENTS

DE    1049864    2/1959
(Continued)

OTHER PUBLICATIONS

Ulmann's Encyclopedia of Industrial Chemistry, 6th Ed., 2000, Electronic Release, Amines, Aliphatic—Cyclic Amines (Karsten Eller, Erhard Henkes, Roland Rossbacher, Hartmut Höke).

*Primary Examiner* — Virginia Manoharan
(74) *Attorney, Agent, or Firm* — Connolly Bove Lodge & Hutz LLP

(57) ABSTRACT

Processes for the continuous fractional distillation of a mixture containing morpholine (MO), monoaminodiglycol (ADG), ammonia and water from a reaction of diethylene glycol (DEG) with ammonia, the process including: (i) separating off ammonia from the mixture at a top of a first distillation column K10; (ii) feeding a bottom fraction from K10 to a second distillation column K20, in which water and an organic product are separated off at the top at a temperature at the top in the range from 45 to 198° C. and a pressure in the range from 0.1 to 15 bar; (iii) feeding a bottom fraction from K20 to a third distillation column K30, wherein the column K30 is a dividing wall column (DWC)which preferably has a dividing wall (DW) in the longitudinal direction of the column to form an upper combined column region (1), a lower combined column region (6), an inflow part (2,4) having an enrichment section (2) and a stripping section (4), and also an offtake part (3,5) having an enrichment section (3) and a stripping section (5), with the bottoms from K20 being fed in in the upper or middle third of the inflow part (2,4), based on the number of theoretical plates of the inflow part, ADG and organic products having a boiling point of >190° C. (1.013 bar) being discharge at the bottom, organic products having a boiling point of $\leq$128° C. (1.013 bar) being discharge at a top and MO being discharge from the middle or lower third of the offtake part (3,5) (side offtake), based on the number of theoretical plates of the offtake part.

41 Claims, 7 Drawing Sheets

U.S. PATENT DOCUMENTS

| | | | |
|---|---|---|---|
| 3,155,657 A | 11/1964 | Bedoit | |
| 3,860,496 A * | 1/1975 | Ginnasi et al. | 203/28 |
| 4,256,880 A | 3/1981 | Frech et al. | |
| 4,739,051 A | 4/1988 | Schroeder et al. | |
| 5,074,967 A * | 12/1991 | Fowlkes | 203/14 |
| 5,530,127 A | 6/1996 | Reif et al. | |
| 6,525,222 B2 | 2/2003 | Nouwen et al. | |
| 7,183,438 B2 | 2/2007 | Gerlach et al. | |
| 2005/0000791 A1* | 1/2005 | Wolfert et al. | 203/43 |
| 2008/0255351 A1 | 10/2008 | Hoffer et al. | |

FOREIGN PATENT DOCUMENTS

| | | |
|---|---|---|
| DE | 3002342 A1 | 2/1981 |
| DE | 3125662 A1 | 1/1983 |
| DE | 102005047458 A1 | 4/2007 |
| EP | 0070397 A1 | 1/1983 |
| EP | 0122367 A2 | 10/1984 |
| EP | 0167872 A2 | 1/1986 |
| EP | 0514692 A2 | 11/1992 |
| EP | 0696572 A1 | 2/1996 |
| EP | 0963975 A1 | 12/1999 |
| EP | 1106600 A2 | 6/2001 |
| WO | WO-03/076386 A2 | 9/2003 |
| WO | WO-2007/036496 A1 | 4/2007 |
| WO | WO-2008/037587 A1 | 4/2008 |
| WO | WO-2008/037589 A1 | 4/2008 |
| WO | WO-2008/037659 A1 | 4/2008 |

\* cited by examiner

METHOD FOR THE CONTINUOUS SEPARATION BY DISTILLATION OF MIXTURES THAT CONTAIN MORPHONLINE (MO), MONOAMINODIGLYCOL (ADG), AMMONIA AND WATER BY MEANS OF DISTILLATION

CROSS-REFERENCE TO RELATED APPLICATIONS

This application is a national stage application, under 35 U.S.C. §371, of PCT/ EP2007/059557, filed Sep. 12, 2007, which claims benefit of European Patent Application No. 06121428.4, filed Sep. 28, 2006.

BACKGROUND OF THE INVENTION

Aminodiglycol (ADG) [=2-(2-aminoethoxy)ethanol=2,2'-aminoethoxyethanol, formula

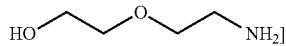

and morpholine are used, inter alia, as solvents, stabilizers, for the synthesis of chelating agents, synthetic resins, drugs, inhibitors and surface-active substances. N-Ethylmorpholine (E-MO) is used, inter alia, as catalyst for the production of polyurethane foams.

Numerous methods of preparing ADG and morpholine are described in the literature.

Ullmann's Encyclopedia of Industrial Chemistry, 6th Edition, 2000 electronic release, Wiley-VCH Verlag, Rubrik 'cyclic amines' in the chapter 'aliphatic amines', describes the synthesis of ADG and MO by amination of DEG under hydrogen pressure and in the presence of a cobalt or nickel catalyst (citations: EP-A-696 572 (BASF AG), DE-A-1 049 864) or other catalysts (citations: DE-A-3 002 342, DE-A-3 125 662 (BASF AG), U.S. Pat. No. 3,155,657).

The earlier German patent application No. 102005047458.6 of Sep. 30, 2005 and the earlier European (subsequent) patent application No. 06101339.7 of Feb. 6, 2006 (BASF AG) relate to a process for preparing ADG and morpholine by reaction of DEG with ammonia in the presence of a specific copper, nickel and cobalt heterogeneous catalyst and also in general terms the work-up by multistage distillation.

Two parallel European patent applications having the same filing date (both BASF AG) relate to processes for the continuous fractional distillation of mixtures comprising morpholine (MO), monoaminodiglycol (ADG), ammonia and water obtained by reaction of diethylene glycol (DEG) with ammonia.

A parallel European patent application having the same filing date (BASF AG) relates to a process for preparing electronics-grade ADG.

The synthesis of morpholine and monoaminodiglycol is notable for the formation of many secondary components. Unreacted starting materials, products of value and the by-products are separated off by distillation, which leads to a considerable outlay in terms of apparatus and energy.

BRIEF SUMMARY OF THE INVENTION

The present invention relates to a process for the continuous fractional distillation of mixtures comprising morpholine (MO), monoaminodiglycol (ADG), ammonia and water obtained by reaction of diethylene glycol (DEG) of the formula

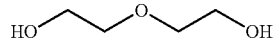

with ammonia.

It was an object of the present invention to overcome a disadvantage or a number of disadvantages of the prior art and discover an improved economical process for the fractionation of mixtures comprising morpholine (MO), monoaminodiglycol (ADG), ammonia and water and possibly N-ethylmorpholine (E-MO) and possibly 1,2-ethylenediamine (EDA) and possibly organic products having a boiling point of >224.8° C. (1.013 bar). The individual organic components (amines), in particular MO and ADG and possibly E-MO, should be obtained in high purity and quality (e.g. color quality).

We have accordingly found a process for the continuous fractional distillation of mixtures comprising morpholine (MO), monoaminodiglycol (ADG), ammonia and water obtained by reaction of diethylene glycol (DEG) with ammonia, which comprises separating off ammonia at the top of a first distillation column K10, feeding the bottoms from K10 to a second distillation column K20 in which water and organic products are separated off at the top at a temperature at the top in the range from 45 to 198° C. and a pressure in the range from 0.1 to 15 bar, feeding the bottoms from K20 to a third distillation column K30, wherein the column K30 is a dividing wall column (DWC) which preferably has a dividing wall (DW) in the longitudinal direction of the column to form an upper combined column region (1), a lower combined column region (6), an inflow part (2, 4) having an enrichment section (2) and a stripping section (4), and also an offtake part (3, 5) having an enrichment section (3) and a stripping section (5), with the bottoms from K20 being fed in in the upper or middle third, particularly preferably the upper third, of the inflow part (2, 4), based on the number of theoretical plates of the inflow part, ADG and organic products having a boiling point of >190° C. (1.013 bar) being discharged at the bottom, organic products having a boiling point of ≦128° C. (1.013 bar), preferably <128° C. (1.013 bar), being discharged at the top and MO being discharged from the middle or lower third, particularly preferably the lower third, of the offtake part (3, 5) (side offtake), based on the number of theoretical plates of the offtake part.

DETAILED DESCRIPTION OF THE INVENTION

The column K10 preferably has from 3 to 30, particularly preferably from 5 to 20, theoretical plates.

It is preferably operated at a pressure in the range from 5 to 30 bar, particularly preferably from 10 to 20 bar.

The feed point of column K10 is preferably located in the upper third, based on the number of theoretical plates.

The column K20 preferably has from 25 to 70, particularly preferably from 30 to 60, theoretical plates.

It is preferably operated at a pressure in the range from 0.1 to 10 bar, particularly preferably from 0.8 to 7 bar.

The feed point of column K20 is preferably located in the middle third, based on the number of theoretical plates.

Water is preferably separated off in the column K20. Organic products, some of which have boiling points higher than that of the bottom product morpholine, are preferably separated off at the top together with this water as a minimum-boiling azeotrope.

The dividing wall column K30 preferably has from 30 to 100, particularly preferably from 40 to 90, theoretical plates.

It is preferably operated at a pressure in the range from 0.01 to 5 bar, particularly preferably from 0.1 to 2.5 bar.

The organic products separated off at the top of the column K30, in particular EDA, can advantageously be recirculated in their entirety or in part to the feed to the column K20.

In a further embodiment, pure EDA can be obtained as product of value by further purification by distillation of the overhead distillate from K30.

The subregion of the column (DWC) divided by the dividing wall (DW) and comprising the subregions 2, 3, 4 and 5 or parts thereof is preferably provided with ordered packing, random packing elements and/or trays. The dividing wall in these subregions is preferably thermally insulating.

In a particular embodiment, the stream comprising water and organic products which is separated off at the top of the column K20 is fed to a column K50 in which aqueous N-ethylmorpholine solution (aqueous E-MO solution) is separated off at the top or at a side offtake for liquid, with the side offtake for liquid preferably being located in the upper third of the column, based on the number of theoretical plates, and water is separated off at the bottom.

The column K50 preferably has from 10 to 50, particularly preferably from 15 to 40, theoretical plates.

It is preferably operated at a pressure in the range from 0.1 to 16 bar, particularly preferably from 0.2 to 8 bar.

The feed point of column K50 is preferably located in the upper or middle third, particularly preferably in the middle third, based on the number of theoretical plates.

To isolate pure E-MO, the aqueous N-ethylmorpholine solution is firstly dewatered. As dewatering agent, preference is given to using sodium hydroxide, e.g. as a 40-60% strength by weight aqueous solution, particularly preferably a 50% strength by weight aqueous solution. The dewatering using the sodium hydroxide is preferably carried out continuously in an extraction column. The extraction temperature is preferably 25-60° C., particularly preferably 30-55° C. The sodium hydroxide solution is diluted to 15-35% by weight, particularly preferably 20-30% by weight, during the extraction.

After phase separation, the organic phase is worked up in a continuous or batch distillation. The distillation is preferably carried out batchwise in a still pot.

In this case, the overhead products are obtained in succession: ethylamine if present, possibly ethanol as aqueous azeotrope, possibly N-methylmorpholine as aqueous azeotrope, possibly water-free N-methylmorpholine and the desired product N-ethylmorpholine (E-MO).

In a preferred embodiment, the bottoms from K30 are fed to a distillation column K60 in which ADG is separated off at a side offtake, organic products having a boiling point of ≦224.8° C. (1.013 bar) are separated off at the top and organic products having a boiling point of >255° C. (1.013 bar) are separated off at the bottom.

The column K60 preferably has from 20 to 80, particularly preferably from 30 to 70, theoretical plates.

It is preferably operated at a pressure in the range from 0.005 to 1 bar, particularly preferably from 0.01 to 0.7 bar.

The feed point of column K60 is preferably located in the middle or lower third, particularly preferably the middle third, based on the number of theoretical plates. The ADG side offtake located opposite the feed point is preferably located from 1 to 30, particularly preferably from 2 to 20, theoretical plates above the feed point.

In a preferred embodiment, organic products separated off at the top of the column K60, e.g. N-(2-aminoethyl)morpholine, 2-(2-aminoethoxy)ethylamine, are recirculated to the reaction of DEG with ammonia.

To avoid accumulation of individual components in the circuit of the production plant, a, substream of the distillate separated off at the top of the column is preferably discharged. The proportion of the recirculated stream is preferably 40-100% by weight, particularly preferably 50-100% by weight, of the distillate separated off at the top of the column.

The organic products separated off at the bottom of the column K60 can advantageously be used as milling aids in the cement industry.

The ADG-comprising stream separated off at the side offtake of the column K60 is preferably fed to a column K70 in which ADG is separated off at a side offtake, organic products having a boiling point of ≧224.8° C. (1.013 bar), particularly preferably >235° C. (1.013 bar), are separated off at the bottom and organic products having a boiling point of ≦224.8° C. (1.013 bar) are separated off at the top.

The column K70 preferably has from 10 to 80, particularly preferably from 20 to 70, theoretical plates.

It is preferably operated at a pressure in the range from 0.005 to 1 bar, particularly preferably from 0.01 to 0.7 bar.

The feed point of column K70 is preferably located in the upper or middle third, preferably the middle third, based on the number of theoretical plates.

The ADG side offtake located opposite the feed point is preferably located from 1 to 30, particularly preferably from 2 to 25, theoretical plates above the feed point.

Products separated off at the bottom of column K70, e.g. DEG,
morpholylaminodiglycol, morpholinodiglycol, are preferably recirculated to the reaction of DEG with ammonia.
(Morpholylaminodiglycol=4-(2-(2-aminoethoxy)ethyl)morpholine, $C_8H_{18}N_2O_2$; morpholinodiglycol (morpholinylethoxyethanol) CAS No. 3603-45-0, $C_8H_{17}NO_3$)

Products separated off at the top of column K70, e.g. ADG, N-(2-aminoethyl)morpholine, 2-(2-aminoethoxy)ethylamine, are preferably recirculated to the reaction of DEG with ammonia.

The proportion of the recirculated stream is preferably 80-100% by weight, particularly preferably 95-100% by weight, of the distillate separated off at the top of the column.

In a further particularly preferred embodiment, the column K60 is a dividing wall column (DWC2).

The dividing wall column (DWC2) preferably has a dividing wall (DW) in the longitudinal direction of the column to form an upper combined column region (1), a lower combined column region (6), an inflow part (2, 4) having an enrichment section (2) and a stripping section (4), and also an offtake part (3, 5) having an enrichment section (3) and a stripping section (5), with the bottoms from K30 being fed in in the upper or middle third, particularly preferably the upper third, of the inflow part (2, 4), based on the number of theoretical plates of the inflow part, organic products having a boiling point of >255° C. (1.013 bar) being discharged at the bottom, organic products having a boiling point of ≦224.8° C. (1.013 bar) being discharged at the top, ADG being discharged from the column region 1 and optionally, in a particular embodiment preferably, gaseous organic products having a boiling point of ≧224.8° C. (1.013 bar), particularly preferably >235° C. (1.013 bar), e.g. DEG, being discharged from the upper or middle third, particularly preferably the upper third, of the offtake part (3, 5) (side offtake), based on the number of theoretical plates of the offtake part.

Organic products separated off in gaseous form at the side offtake of the column K60, e.g. DEG, are preferably recirculated to the reaction of DEG with ammonia.

In a further advantageous embodiment, the dividing wall column (DWC2) has a dividing wall (DW) in the longitudinal direction of the column to form an upper combined column region (1) and (2), an inflow part (3, 4) having an enrichment section (3) and a stripping section (4), and also a part (5), with the dividing wall DW extending to the bottom of the column and the bottoms from K30 being fed in in the upper or middle third, particularly preferably the upper third, of the inflow part (3, 4), based on the number of theoretical plates of the inflow part, DEG and organic products having a boiling point of ≧224.8° C. (1.013 bar), preferably >235° C. (1.013 bar), being discharged at the bottom below the part 5, organic products having a boiling point of >255° C. (1.013 bar) (high boilers=HB) being discharged at the bottom below the parts 3 and 4, organic products having a boiling point of ≦224.8° C. (1.013 bar) being discharged at the top and ADG being discharged from the middle part of the upper combined column region (1) and (2) (side offtake).

The dividing wall column K60 preferably has from 30 to 100, particularly preferably from 40 to 90, theoretical plates.

It is preferably operated at, a pressure in the range from 0.005 to 1 bar, particularly preferably from 0.01 to 0.7 bar.

The subregion of the column (DWC2) divided by the dividing wall (DW) and comprising the subregions 3, 4 and 5 or 2, 3, 4 and 5 or in each case parts thereof is preferably provided with ordered packing, random packing elements and/or trays. The dividing wall in these subregions is preferably thermally insulating.

In a preferred embodiment, organic products separated off at the top of the column K60, e.g. N-(2-aminoethyl)morpholine, 2-(2-aminoethoxy)ethylamine, are not discharged from the process but are recirculated to the reaction of DEG with ammonia.

Organic products separated off at the bottom below the part 5 of column K60 having a dividing wall DW extending to the bottom of the column, e.g. DEG, are preferably recirculated to the reaction of DEG with ammonia.

The proportion of the recirculated stream is preferably 80-100% by weight, particularly preferably 95-100% by weight, of the distillate separated off at the top of the column.

In particular embodiments using the further dividing wall column (DWC2), the process of the invention also advantageously displays an even lower heat requirement compared to the 2- or 3-column arrangement (K60-K70 or K80) and a further reduced number of columns.

In a particular embodiment of the process of the invention, the ADG-comprising stream/streams separated off at the top of the columns K60 and/or K70 is/are fed in its/their entirety or in part to a column K80 in which ADG and organic products having a boiling point of ≧224.8° C. (1.013 bar) are separated off at the bottom and organic products having a boiling point of ≦224.8° C. (1.013 bar) are separated off at the top.

The ADG obtained at the bottom can be utilized as product of value.

ADG in particularly pure form is preferably additionally separated off at a side offtake of the column K80.

In this case, products separated off at the bottom of column K80 are preferably recirculated to the feed to the columns K60 and/or K70.

Products separated off at the top of column K80 are preferably recirculated to the reaction of DEG with ammonia.

To avoid accumulation of individual components in the circuit of the production plant, a substream of the distillate separated off at the top of the column is preferably discharged. The proportion of the recirculated stream is preferably 0-100% by weight, particularly preferably 0-50% by weight, of the distillate separated off at the top of the column.

The column K80 preferably has from 10 to 80, particularly preferably from 15 to 60, theoretical plates.

It is preferably operated at a pressure in the range from 0.005 to 3 bar, particularly preferably from 0.01 to 2 bar.

The feed point of column K80 is preferably located in the upper or middle third, preferably the upper third, based on the number of theoretical plates.

The ADG side offtake located opposite the feed point is preferably located from 1 to 30, particularly preferably from 2 to 25, theoretical plates below the feed point.

In particular embodiments, the process of the invention is additionally advantageous as a result of the following heat integration measures:

The heat from the vapor from K80 can be integrated into K50.

The heat from the vapor from K70 can be integrated into K50 and/or K80, preferably K50.

The heat from the vapor from K60 can be integrated into K50.

The heat from the vapor from the dividing wall column K60 can be integrated into K50.

This heat integration can be effected as follows:

To be able to make maximum use of the heat obtained from the vapor, a heat transfer medium is preferably dispensed with and the vapor streams are preferably condensed directly in the corresponding vaporizers instead of heating steam. As vaporizers, it is in each case possible to use natural convection vaporizers, forced circulation vaporizers, forced circulation depressurization vaporizers, falling film evaporators, Robert evaporators, kettle-type vaporizers, thin film evaporators or climbing film evaporators. Preference is in each case given to using natural convection vaporizers, forced circulation vaporizers, forced circulation depressurization vaporizers, falling film evaporators, Robert evaporators or kettle-type vaporizers.

The residual vapors are preferably in each case liquefied in an after-condenser.

Furthermore, it is advantageous for the heat of reaction from the synthesis of the mixture to be fractionated to be removed, in particular by evaporative cooling (steam), and integrated into the distillation. Embodiments (A) and (B) are particularly preferred in the synthesis.

The heat of reaction can here be integrated into the columns K20, K50, K30, K70 and/or K80, preferably into the columns K20, and/or K80.

The mixture comprising morpholine (MO), monoaminodiglycol (ADG), ammonia and water, and possibly E-MO and possibly EDA and possibly organic products having a boiling point of >224.8° C. (1.013 bar) which is used in the process of the invention has, in an embodiment (A), preferably been obtained by reaction of diethylene glycol (DEG) with ammonia in the presence of a catalyst comprising Cu, Ni and Co on zirconium dioxide as support.

Catalysts of this type are described in EP-A-963 975, EP-A-1 106 600 and WO-A-03/076386 (all BASF AG).

In a particularly preferred catalyst, the catalytically active composition of the catalyst before treatment with hydrogen comprises from 20 to 65% by weight of zirconium dioxide ($ZrO_2$), from 1 to 30% by weight of oxygen-comprising compounds of copper, calculated as CuO, from 15 to 50% by weight of oxygen-comprising compounds of nickel, calculated as NiO, and from 15 to 50% by weight of oxygen-comprising compounds of cobalt, calculated as CoO.

The temperature in the reactor which is preferred for the reaction of diethylene glycol (DEG) with ammonia is in the range from 170 to 220° C. Preference is given to isothermal operation of the reactor. The pressure preferred for the reaction of diethylene glycol (DEG) with ammonia is in the range from 100 to 200 bar.

The reaction of diethylene glycol (DEG) with ammonia is preferably carried out in the presence of hydrogen. The hydrogen is preferably recirculated as recycle gas via a high-pressure separator to the reactor.

The molar ratio of ammonia:DEG is preferably in the range from 4 to 6.

The DEG conversion is preferably in the range from 55 to 90%.

The mixture used in the process of the invention is particularly preferably produced as described in the earlier German patent application No. 102005047458.6 of Sep. 30, 2005 and the earlier European (subsequent) patent application No. 06101339.7 of Feb. 6, 2006 (BASF AG), according to which the reaction of DEG with ammonia is carried out in the presence of a specific shaped catalyst body and the catalytically active composition of the catalyst before treatment with hydrogen comprises oxygen-comprising compounds of aluminum and/or zirconium, copper, nickel and cobalt.

In another embodiment (B), the mixture comprising morpholine (MO), monoaminodiglycol (ADG), ammonia and water, and possibly E-MO and possibly EDA and possibly organic products having a boiling point of >224.8° C. (1.013 bar), which is used in the process of the invention has preferably been obtained by reaction of diethylene glycol (DEG) with ammonia in the presence of a catalyst comprising Cu and Ni on aluminum oxide as support, as described, in particular, in EP-A-70 397 (BASF AG).

Catalysts of this type are also described in EP-A-514 692 and EP-A-167 872 (both BASF AG).

In a catalyst which is particularly preferred here, the catalytically active composition of the catalyst before treatment with hydrogen comprises from 25 to 65% by weight of aluminum oxide ($Al_2O_3$), from 30 to 60% by weight of oxygen-comprising compounds of copper, calculated as CuO, and from 5 to 15% by weight of oxygen-comprising compounds of nickel, calculated as NiO.

The temperature in the reactor which is preferred for the reaction of diethylene glycol (DEG) with ammonia is in this case in the range 190-235° C. Preference is given to isothermal operation of the reactor. The pressure preferred for the reaction of diethylene glycol (DEG) with ammonia is in the range from 20 to 30 bar.

The reaction of diethylene glycol. (DEG) with ammonia is preferably carried out in the gas phase in the presence of hydrogen. The gaseous output from the reactor is preferably fed to a heat exchanger in which a partial condensation is preferably carried out (condensation of crude morpholine). The gas phase comprising $H_2$ and $NH_3$ is preferably conveyed back to the DEG vaporizer and then into the reactor.

The process of the invention is particularly advantageous for preparing morpholine (MO)
having a purity of ≧99.5% by weight, particularly preferably ≧99.6% by weight, e.g. from 99.65 to 99.95% by weight,
an N-ethylmorpholine (E-MO) content of ≦0.20% by weight, particularly preferably ≦0.10% by weight, e.g. from 0.01 to 0.08% by weight,
a 1,2-ethylenediamine (EDA) content of ≦0.30% by weight, particularly preferably ≦0.20% by weight, e.g. from 0.05 to 0.15% by weight,
a 2-methoxyethanol content of <0.50% by weight, particularly preferably <0.30% by weight, e.g. from 0.05 to 0.25% by weight,
and a water content of ≦0.05% by weight, particularly preferably ≦0.04% by weight, e.g. from 0.01 to 0.03% by weight.

It is very particularly preferably advantageous for preparing morpholine (MO) having an APHA color number of ≦10, particularly preferably ≦8, e.g. from 2 to 7,
and a chloride content of ≦15 mg/liter, particularly preferably ≦5 mg/liter, very particularly preferably ≦1 mg/liter, e.g. from 0.1 to 0.9 mg/liter.

The process of the invention is also particularly advantageous for preparing monoaminodiglycol (ADG) having a purity of ≧98.00% by weight, particularly preferably ≧98.30% by weight, e.g. from 98.50 to 99.50% by weight,
a DEG content of ≦0.40% by weight, particularly preferably ≦0.10% by weight, e.g. from 0.01 to 0.08% by weight,
a water content of ≦0.20% by weight, particularly preferably ≦0.10% by weight, e.g. from 0.01 to 0.08% by weight,
and an APHA color number of ≦20, particularly preferably ≦15, very particularly preferably ≦10, e.g. from 2 to 8.

The process of the invention is also particularly advantageous for preparing N-ethyl-morpholine (E-MO) having a purity of ≧98.50% by weight, particularly preferably ≧99.00% by weight, e.g. from 99.50 to 99.90% by weight,
a water content of ≦0.30% by weight, particularly preferably ≦0.20% by weight, e.g. from 0.05 to 0.15% by weight,
and an APHA color number of ≦50, particularly preferably ≦20, very particularly preferably ≦10, e.g. from 2 to 8.

APHA color numbers are determined in accordance with DIN EN 1557.

The water content is determined in accordance with DIN 51777 (K. Fischer).

The chloride content is determined by means of ion chromatography (detection of conductivity with chemical suppression), using the following method:

Sample preparation: about 2 g of sample are weighed into a volumetric flask (10 ml) and made up to the mark with eluent.

Measurement conditions:

Ion chromatography system: Metrohm Modulares System (733)

Preliminary column: e.g. DIONEX AG 12; separation column: e.g. DIONEX AS 12

Eluent: e.g. 2.7 mmol of $Na_2CO_3$, 0.28 mmol/l of $NaHCO_3$ in water

Flow: 1 ml/min; injection volume: 100 μl

Detection: conductivity after chemical suppression

Suppressor: Metrohm Modul 753

Regenerent: 50 mmol of $H_2SO_4$ in high-purity water (flow about 0.4 ml/min)

Calibration: external, checked by standard addition experiments

Determination limit: 0.1 mg/kg of chloride in the sample.

In the desired product morpholine, the content of morpholine, 1,2-ethylenediamine, N-ethylmorpholine, 2-methoxyethanol is determined by means of GC (GC conditions: 30 m DB-1; temperature program with 60° C. initial temperature, 4° C./min heating rate, 190° C. final temperature).

In the desired product ADG, the content of ADG and DEG is determined by means of GC (GC conditions: 30 m DB1, temperature program with 100° C. initial temperature, 8° C./min heating rate, 250° C. final temperature).

HB=high boilers, LB=low boilers, IB=intermediate boilers, WWT=wastewater requiring treatment.

EXAMPLES

Figure 1:
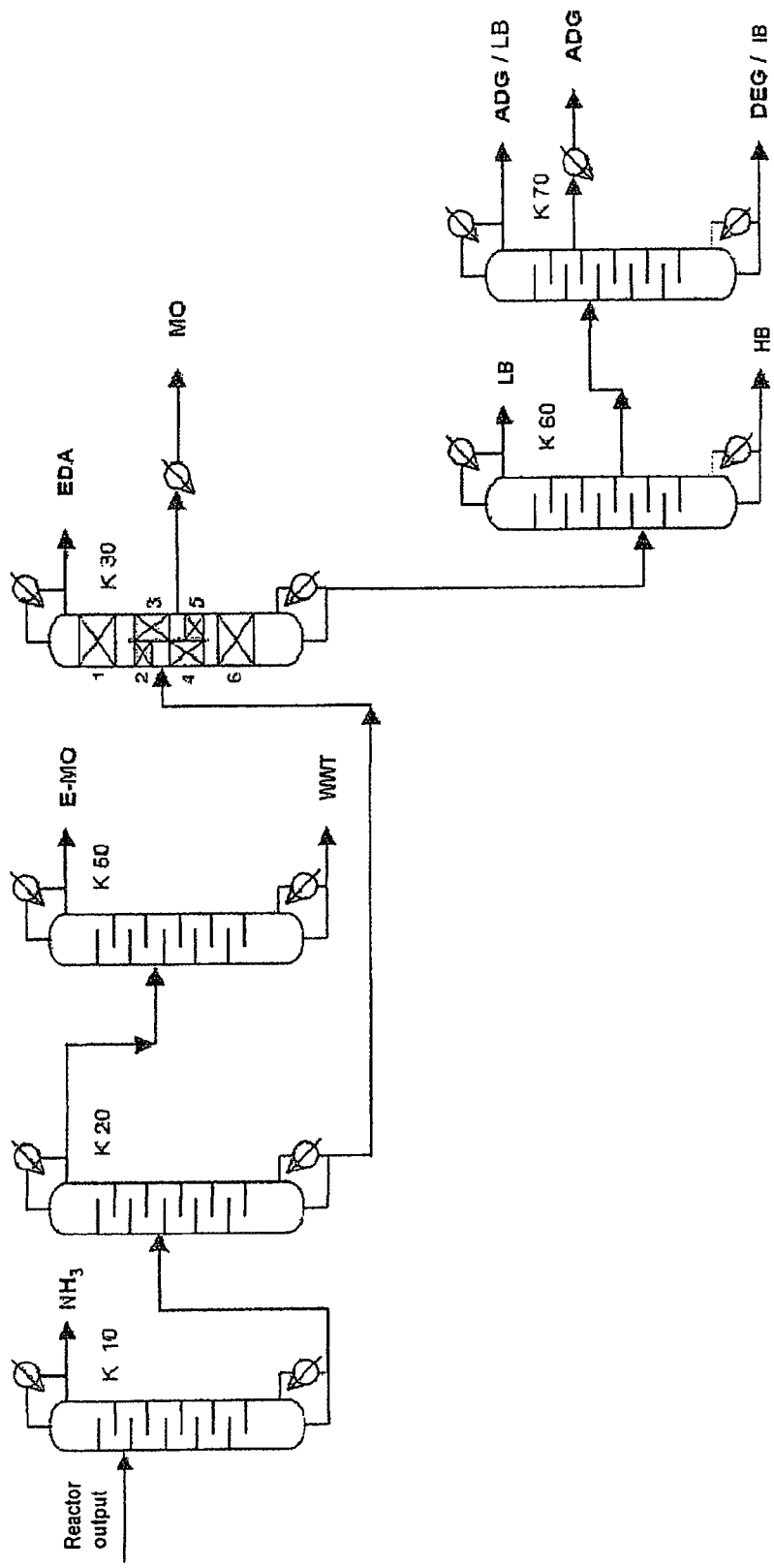
FIG. 1 shows, inter alia, the isolation of MO and ADG according to the invention by means of a 6-column arrangement.
Figure 2:
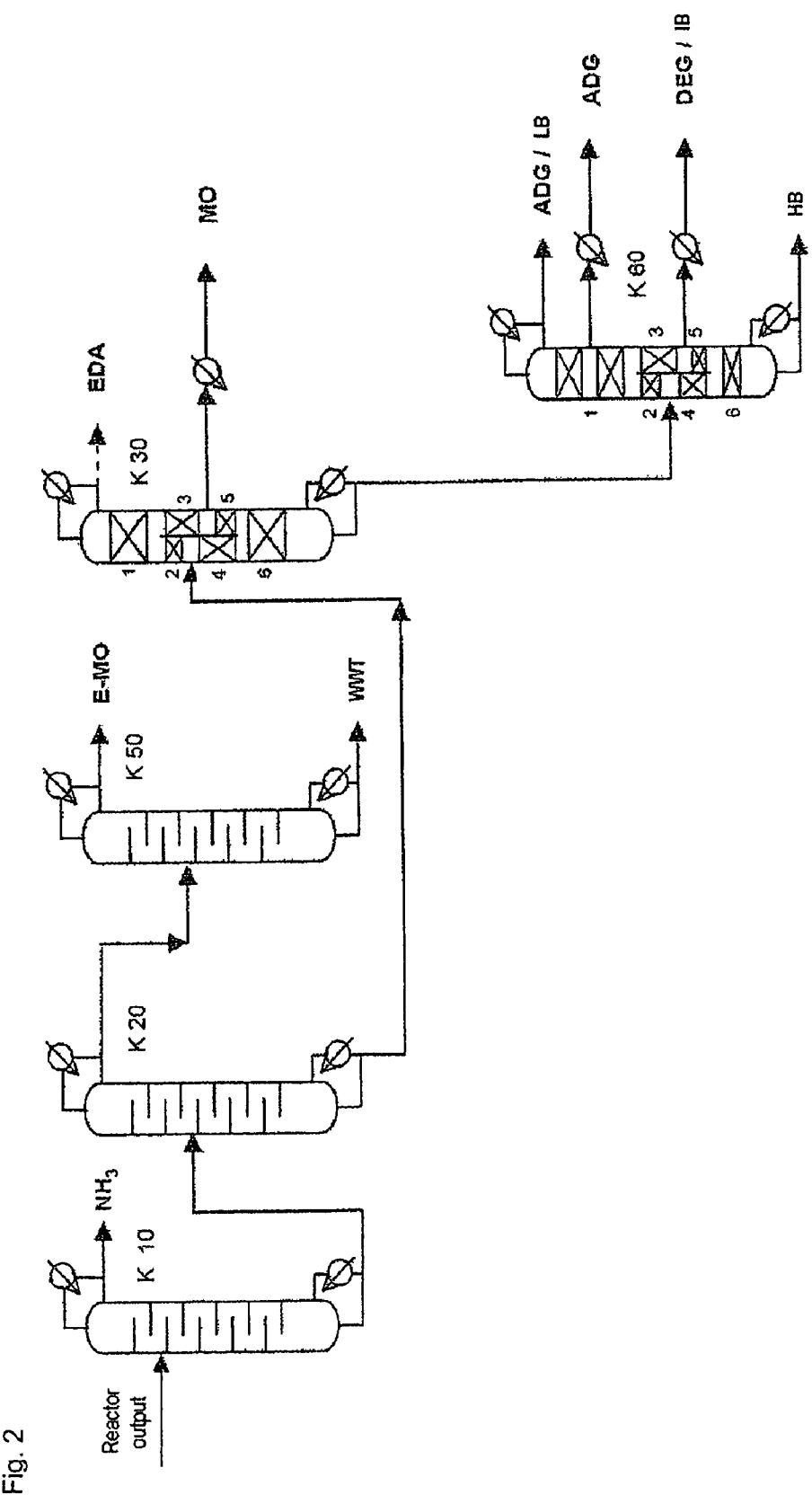
FIG. 2 shows, inter alia, the replacement of the columns K60-K70 of the 6-column arrangement by a dividing wall column (DWC2).
Figure 3:
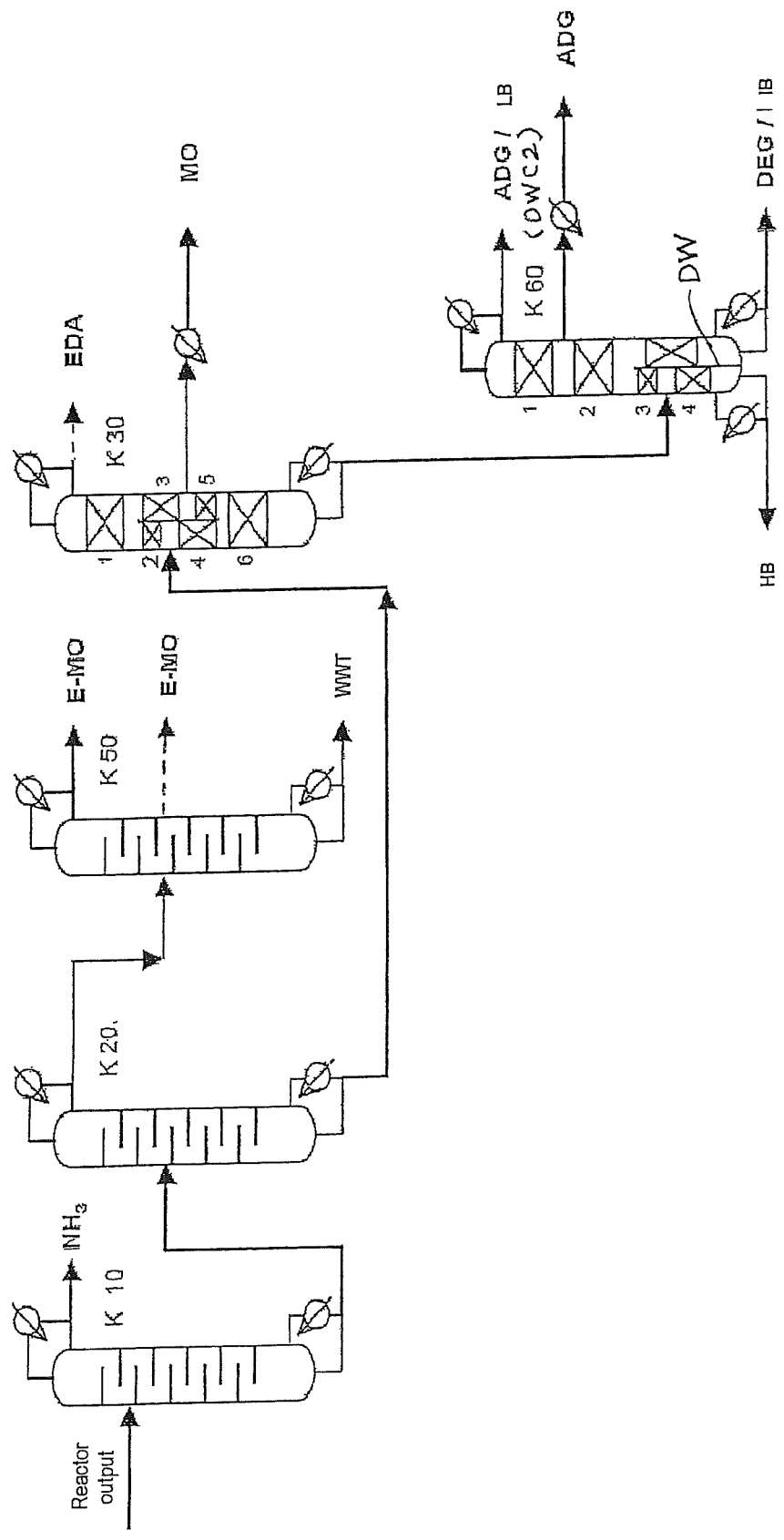
FIG. 3 shows, inter alia, a particular embodiment of the dividing wall column K60 in which the dividing wall (DW) extends to the bottom of the column.
Figure 4:
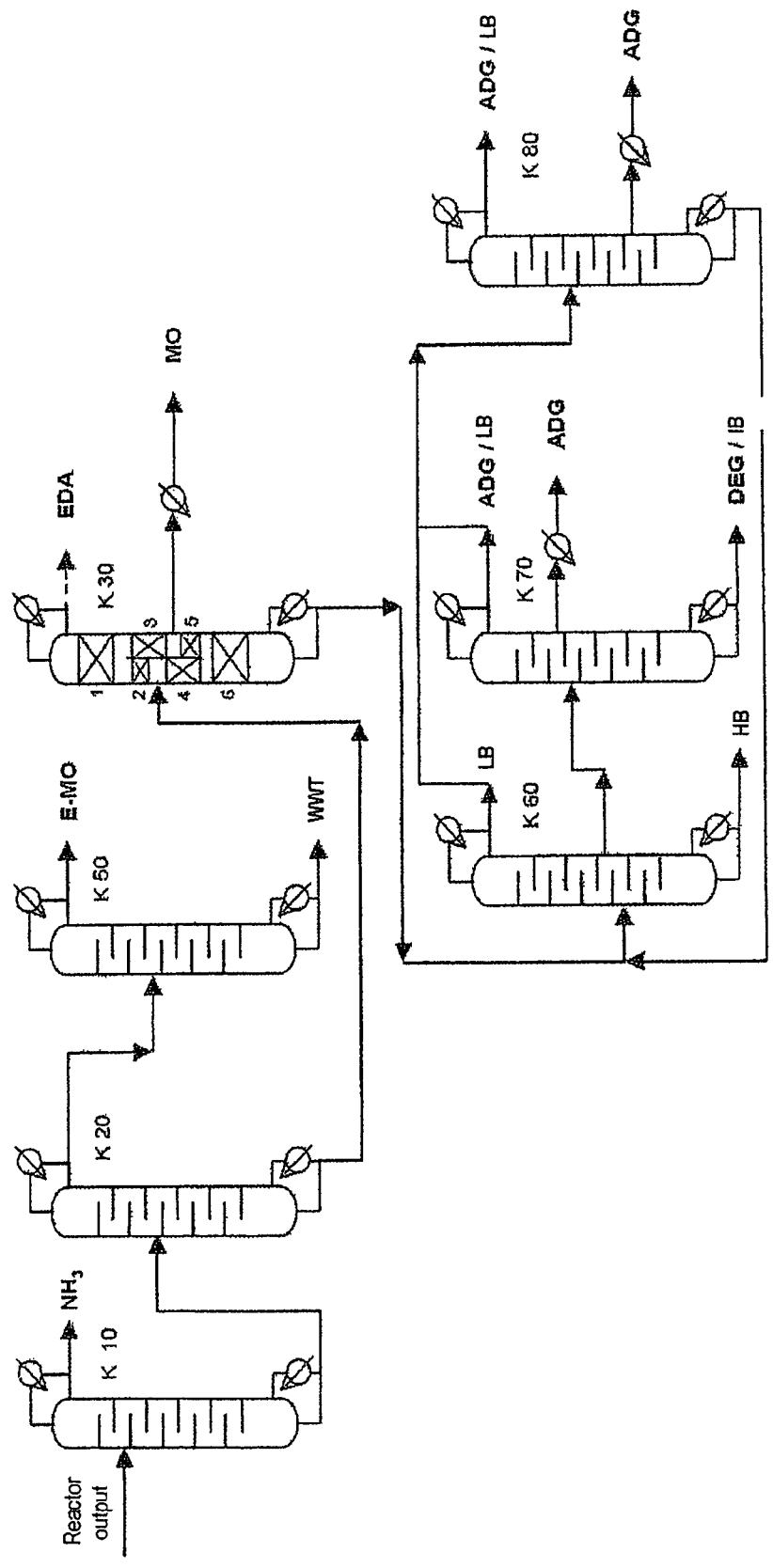
FIG. 4 shows, inter alia, the isolation of MO according to the invention and an additional column (K80) for isolating ADG in particularly pure form.
Figure 5:
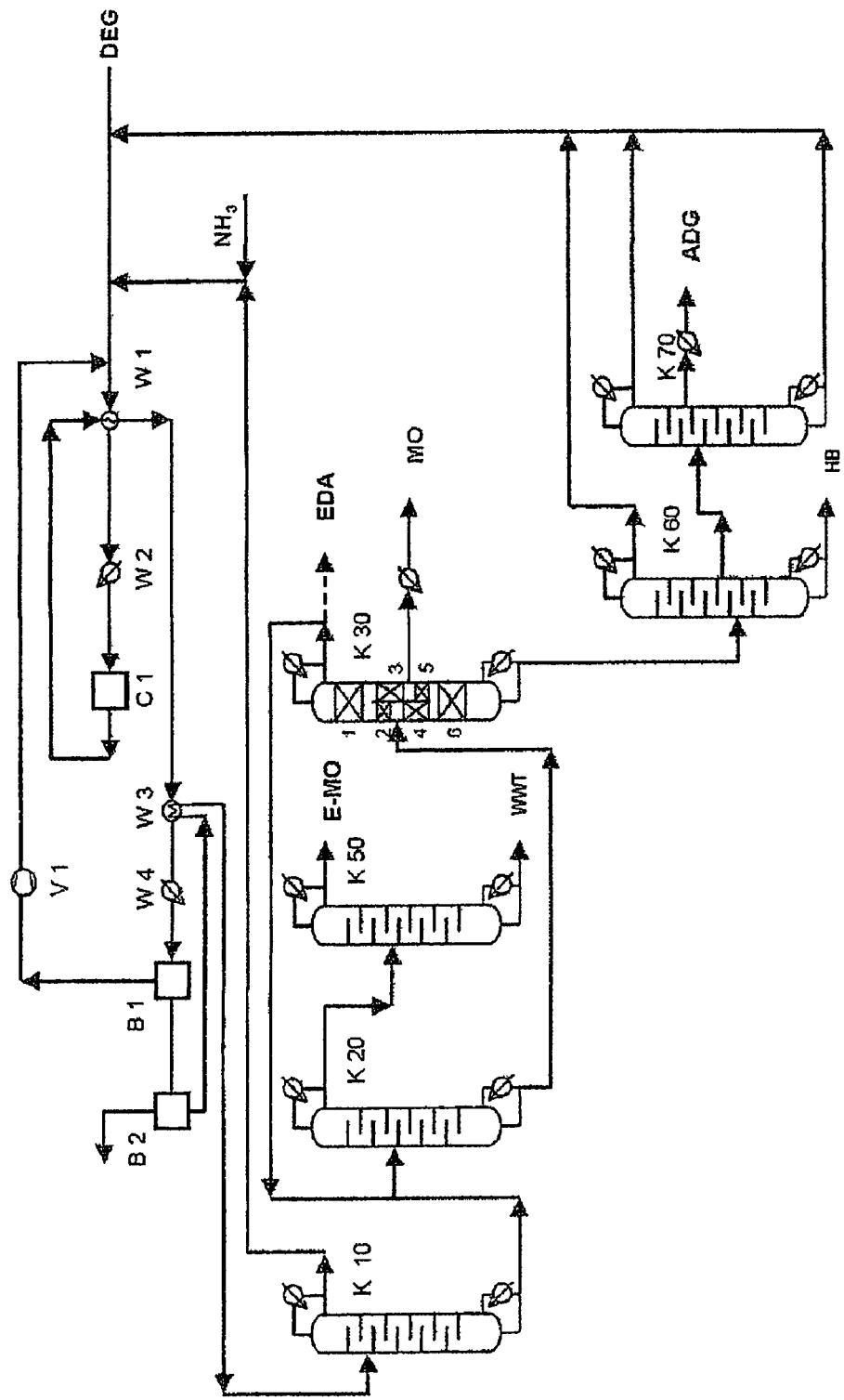
FIG. 5 shows, inter alia, by way of example, the 6-column arrangement as used in the example, including recycle streams and synthesis part and heat integration (B1=high-pressure separator, B2=intermediate-pressure separator, C1=reactor, V1=compressor, W1,2,3 and 4=heat exchangers).
Figure 6:
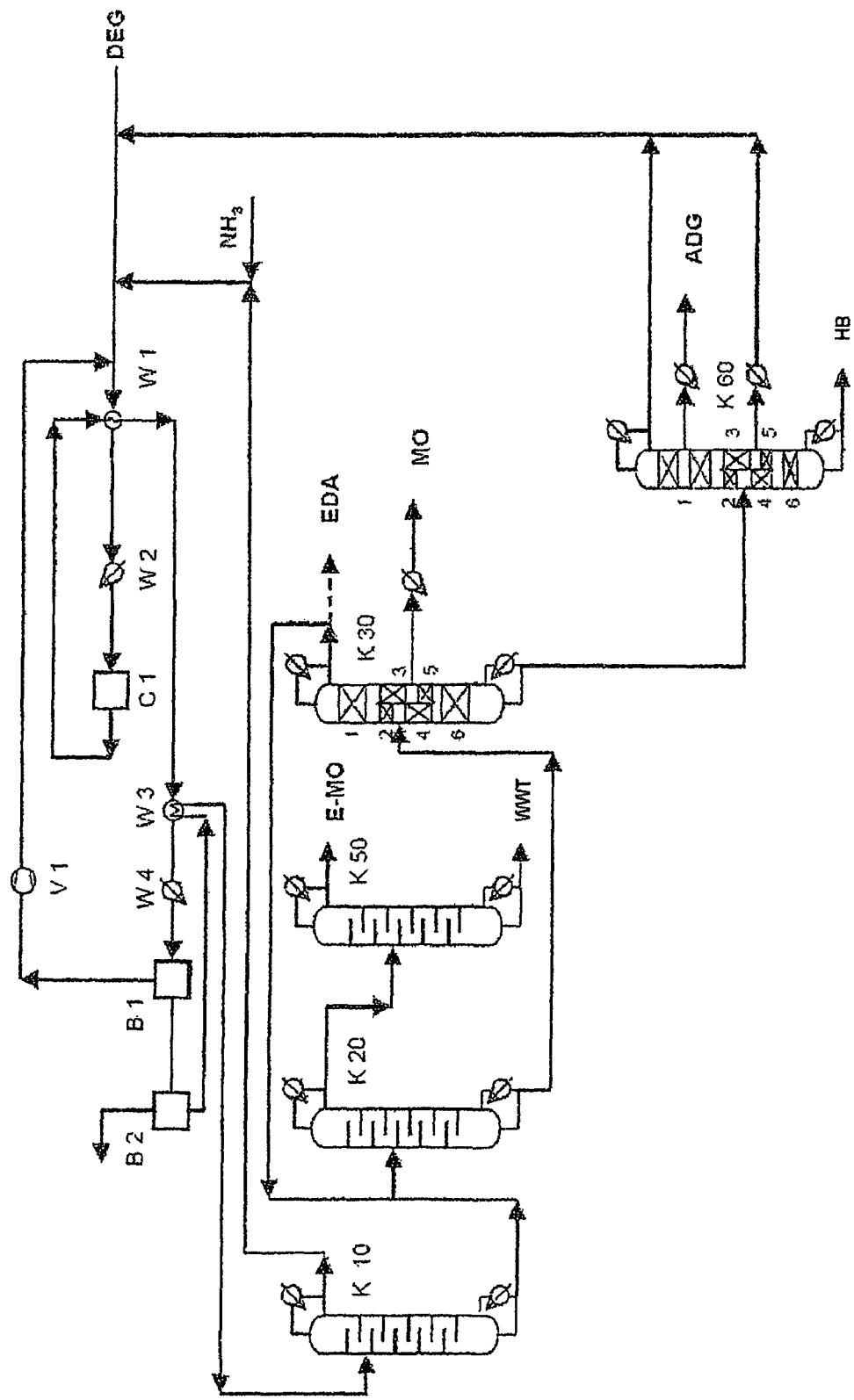
FIG. 6 shows, inter alia, by way of example, an embodiment including recycle streams and synthesis part and heat integration in which the columns K60-K70 of the 6-column arrangement are replaced by a dividing wall column (DWC2).
Figure 7:
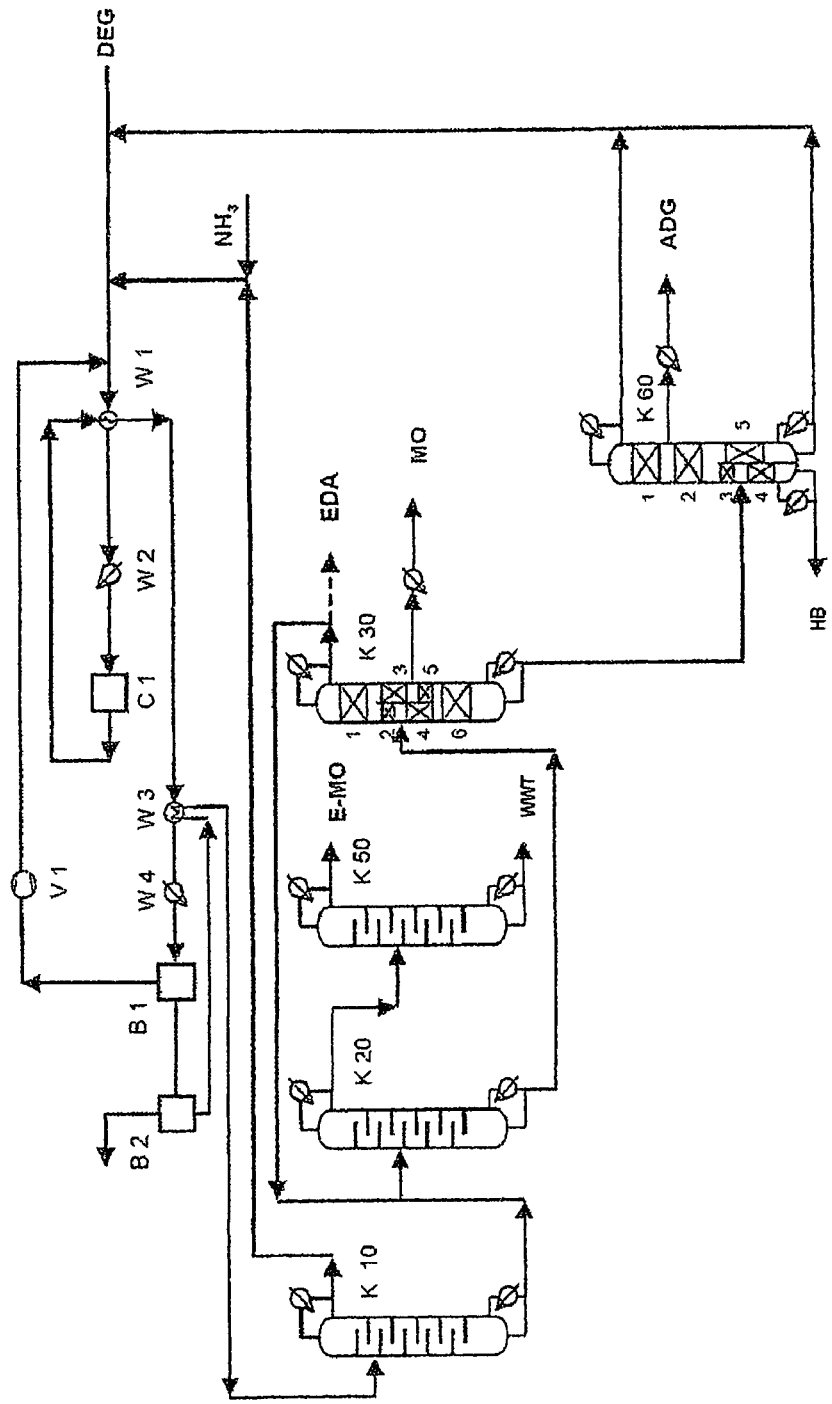
FIG. 7 shows, inter alia, by way of example, an embodiment including recycle streams and synthesis part and heat integration in which the dividing wall (DW) extends to the bottom of the column.

Example 1 (see FIG. 5)

Diglycol (DEG) is mixed with the bottom product from the column K70 (main components: diglycol and morpholyl-ADG) and the overhead products from the columns K60 and K70 (main components: aminodiglycol, (2-aminoethyl)morpholine and 2-(2-aminoethoxy)ethylamine) and fed continuously to the heat exchanger W 1. Liquid ammonia is mixed with recirculated ammonia from the column K10 and fed continuously to the heat exchanger W 1.

Both streams are mixed with the recycle gas consisting predominantly of hydrogen upstream of the heat exchanger W 1. The recycle gas is brought from the high-pressure separator B 1 located at the outlet from the synthesis by means of the compressor V 1. After the heat exchanger W 1, the mixture which has a temperature of 140° C. is heated to 175° C. by means of a heater W 2 and conveyed to the reactor C 1.

The reaction of the diglycol to form aminodiglycol and morpholine takes place over the fixed-bed catalyst there at a pressure of 200 bar and temperatures up to 215° C. The output from the reactor is then cooled to 45° C. in the heat exchangers W 1, W 3 and the air cooler W 4. In the high-pressure separator B 1, separation into a gas phase and a liquid phase occurs. The gas phase is, as described above, conveyed as recycle gas to the heat exchanger W 1.

The liquid phase from the high-pressure separator B 1 is depressurized to 25 bar into the intermediate-pressure separator B 2. The gas liberated there from the effervescing liquid is conveyed into an absorber to recover $NH_3$. The amount of hydrogen to be replaced is taken from the network and introduced into the feed to the synthesis.

The reaction mixture then goes from the intermediate-pressure separator B 2 via the heat exchanger W 3 to the column K10.

Ammonia Removal (K10)

In the column K10, the ammonia is distilled off at a purity of >99.9% from the feed at a pressure at the top of 16 $bar_{abs.}$ and recirculated to the reactor inlet. The offgas is connected to an absorber. The ammonia-free bottoms having a temperature of 220° C. are depressurized into the column K20 for the removal of water. K10 has 17 theoretical plates and the feed point is at plate 14.

Water Removal (K20)

In the column K20, the water of reaction is separated off at atmospheric pressure. The distillate, which comprises 98% by weight of water and 2% by weight of low boilers (predominantly ethylmorpholine), is fed to the column K50. In addition, the overhead product of the pure morpholine distillation K40 (main components: 1,2-ethylenediamine, morpholine and water) is fed to the column K20. The largely water-free bottoms from K20 are depressurized at a temperature of 158° C. (main components: morpholine, aminodiglycol, diglycol and high-boiling residue) into the column K30. K20 has 56 theoretical plates and the feed point is at plate 25.

Pure Morpholine Distillation (K30)

In the dividing wall column K30, morpholine (MO) having a concentration of >99.6% by weight of morpholine and a 1,2-ethylenediamine (EDA) content of <0.10% by weight is separated off in gaseous form at a side offtake in the lower third of the offtake part (3, 5), based on the number of theoretical plates of the offtake part, at a pressure at the top of 550 mbar. The overhead distillate (main components: 1,2-ethylenediamine, morpholine and water) is recirculated to K20 or, after concentration of ethylenediamine, discharged discontinuously via a container. The bottoms from the column K30 (main components: aminodiglycol, diglycol and high-boiling residue), which have a temperature of 217° C., are recirculated to the column K60.

The dividing wall column which has a dividing wall (DW) in the longitudinal direction of the column has 33 theoretical plates in the upper combined column region (1), 6 theoretical plates in the lower combined column region (6) and 21 theoretical plates in the inflow part (2, 4) and in the offtake part (3, 5). The bottoms from K20 are fed in in the upper third of the inflow part (2, 4) at plate 18 of 21 and MO is discharged from the lower third of the offtake part (3, 5) at plate 9 of 21.

Ethylmorpholine Distillation (K50)

In the column K50, N-ethylmorpholine is separated off from the feed as an azeotrope with water at atmospheric pressure. The bottoms from the column, which have a temperature of 103° C., are discharged. K50 has 21 theoretical plates and the feed point is at plate 11.

Residue Removal (K60)

In the column K60, aminodiglycol and diglycol are separated off together from the feed as a liquid side offtake stream at a pressure at the top of 60 mbar and are conveyed to the column K70. The distillate from the column (main components: aminoethoxy-ethylamine, aminoethylmorpholine, aminodiglycol) is recirculated to the reactor inlet. The bottoms from the column, which have a bottoms temperature of 204° C., are discharged from the process. K60 has 42 theoretical plates/feed point at plate 20/side offtake at plate 36.

Aminodiglycol Distillation (K70)

In the column K70, aminodiglycol having a purity of >98.0% by weight and a water content <0.10% by weight is separated off from the feed as a liquid side offtake stream at a pressure at the top of 80 mbar. The condensate from the column (main components: aminodiglycol, (2-aminoethyl) morpholine and 2-(2-aminoethoxy)ethylamine) is recirculated to the reactor inlet. The bottoms from the column (87% by weight of DEG, 11% by weight of morpholyl-ADG and 2% by weight of high boilers), which have a bottoms temperature of 238° C., are likewise recirculated to the reactor inlet. K70 has 42 theoretical plates, the feed point is at plate 25 and the side offtake is at plate 35.

The numbering of the plates in the columns is from the bottom upward.

The invention claimed is:

1. A process for the continuous fractional distillation of a mixture comprising morpholine (MO), monoaminodiglycol (ADG), ammonia and water from a reaction of diethylene glycol (DEG) with ammonia, the process comprising:
separating off ammonia from the mixture at a top of a first distillation column K10;
feeding a bottom fraction from K10 to a second distillation column K20 in which water and organic products are separated off at the top at a temperature at the top in the range from 45 to 198° C. and a pressure in the range from 0.1 to 15 bar,
feeding a bottom fraction from K20 to a third distillation column K30, wherein the column K30 is a dividing wall column (DWC) which preferably has a dividing wall (DW) in the longitudinal direction of the column to form an upper combined column region (1), a lower combined column region (6), an inflow part (2, 4) having an enrichment section (2) and a stripping section (4), and also an offtake part (3, 5) having an enrichment section (3) and a stripping section (5), with the bottoms from K20 being fed in in the upper or middle third of the inflow part (2, 4), based on the number of theoretical plates of the inflow part, ADG and organic products having a boiling point of >190° C. (1.013 bar) being discharged at the bottom, organic products having a boiling point of ≦128° C. (1.013 bar) being discharged at the top and MO being discharged from the middle or lower third of the offtake part (3, 5) (side offtake), based on the number of theoretical plates of the offtake part.

2. The process according to claim 1, wherein at least a portion of the organic products separated off at the top of column K30 are recirculated to the feed to the column K20.

3. The process according to claim 1, wherein the column K10 has from 3 to 30 theoretical plates and is operated at a pressure of 5 to 30 bar.

4. A process according to claim 1 wherein the column K20 has from 25 to 70 theoretical plates and is operated at a pressure of 0.1 to 10 bar.

5. The process according to claim 1, wherein the dividing wall column K30 has from 30 to 100 theoretical plates and is operated at a pressure of 0.01 to 5 bar.

6. The process according to claim 1, wherein the feed point of column K10 is located in the upper third, based on the number of theoretical plates.

7. The process according to claim 1, wherein the feed point of column K20 is located in the middle third, based on the number of theoretical plates.

8. The process according to claim 1, wherein the subregion of the column (DWC) divided by the dividing wall (DW) and comprising the subregions 2,3,4 and 5 or parts thereof is provided with order packing, random packing element and/or trays and the dividing wall in these subregions is thermally insulating.

9. The process according to claim 1, wherein the stream comprising water and organic products which is separated off at the top of the column K20 is fed to a column K50 in which aqueous N-ethylmorpholine solution (aqueous E-MO solution) is separated off at the top or at a side offtake for liquid and water is separated off at the bottom.

10. The process according to claim 9, wherein the column K50 has from 10 to 50 theoretical plates and is operated at a pressure of 0.01 to 16 bar.

11. The process according to claim 9, wherein the feed point of column K50 is located in the upper or middle third, based on the number of theoretical plates.

12. The process according to claim 9, wherein the aqueous N-ethylmorpholine solution is dewatered and the organic phase formed here is then concentrated by distillation to give the desired product.

13. The process according to claim 1, wherein the bottoms from K30 are fed to a distillation column K60 in wich ADG is separated off at a side offtake, organic products having a boiling point of ≦224.8° C. (1.013 bar) are separated off at the top and organic products having a boiling point of >255° C. (1.013 bar) are separated off at the bottom.

14. The process according to claim 13, wherein the column K60 has from 20 to 80 theoretical plates and is operated at a pressure of 0.005 to 1 bar.

15. The process according to claim 13, wherein the feed point of column K60 is located in the middle or lower third, based on the number of theoretical plates, and the ADG side offtake located opposite the feed point is located from 1 to 30 theoretical plates above the feed point.

16. The process according to claim 13, wherein organic products separated off at the top of the column K60 are discharged or recirculated to the reaction of DEG with ammonia.

17. The process according to claim 13, wherein the ADG-comprising stream separated off at the side offtake of the column K60 is fed to a column K70 in which ADG is separated off at a side offtake, organic products having a boiling point of ≧224.8° C. (1.013 bar) are separated off at the bottom and organic products having a boiling point of ≦224.8° C. (1.013 bar) are separated off at the top.

18. The process according to claim 17, wherein the column K70 has from 10 to 80 theoretical plates and is operated at a pressure of 0.005 to 1 bar.

19. The process according to claim 17, wherein the feed point of column K70 is located in the upper or middle third, based on the number of theoretical plates, and the ADG side offtake located opposite the feed point is located from 1 to 30 theoretical plates above the feed point.

20. The process according to claim 17, wherein products separated off at the bottom of column K70 are recirculated to the reaction of DEG with ammonia.

21. The process according to claim 17, wherein products separated off at the top of column K70 are recirculated to the reaction of DEG with ammonia.

22. The process according to claim 13, wherein the column K60 is a dividing wall column (DWC2).

23. The process according to claim 22, wherein the dividing wall column (DWC2) has a dividing wall (DW) in the longitudinal direction of the column to form an upper combined column region (1), a lower combined column region (6), an inflow part (2, 4) having an enrichment section (2) and a stripping section (4), and also an offtake part (3, 5) having an enrichment section (3) and a stripping section (5), with the bottoms from K30 being fed in in the upper or middle third of the inflow part (2, 4), based on the number of theoretical plates of the inflow part, organic products having a boiling point of >255° C. (1.013 bar) being discharged at the bottom, organic products having a boiling point of ≦224.8° C. (1.013 bar) being discharged at the top, ADG being discharged from the column region 1 and optionally gaseous organic products having a boiling point of ≧224.8° C. (1.013 bar) being discharged from the upper or middle third of the offtake part (3, 5) based on the number of theoretical plates of the offtake part.

24. The process according to claim 23, wherein products separated off in gaseous form at the side offtake are recirculated to the reaction of DEG with ammonia 25. The process according to claim 22, wherein the dividing wall column (DWC2) has a dividing wall (DW) in the longitudinal direction of the column to form an upper combined column region (1) and (2), an inflow part (3, 4) having an enrichment section (3) and a stripping section (4), and also a part (5), with the dividing wall DW extending to the bottom of the column and the bottoms from K30 being fed in in the upper or middle third of the inflow part (3, 4), based on the number of theoretical plates of the inflow part, DEG and organic products having a boiling point of $\geq 224.8°$ C. (1.013 bar) being discharged at the bottom below the part 5, organic products having a boiling point of $>255°$ C. (1.013 bar) being discharged at the bottom below the parts 3 and 4, organic products having a boiling point of $\leq 224.8°$ C. (1.013 bar) being discharged at the top and ADG being discharged from the middle part of the upper combined column region (1) and (2).

26. The process according to claim 25, wherein product separated off at the bottom below the part 5 are recirculated to the reaction of DEG with ammonia.

27. The process according to claim 22, wherein the dividing wall column K60 has from 30 to 100 theoretical plates and is operated at a pressure of 0.005 to 1 bar.

28. The process according to claim 22, wherein the dividing wall is thermally insulating.

29. The process according to claim 22, wherein organic products separated off at the top are recirculated to the reaction of DEG with ammonia.

30. The process according to claim 13, wherein at least a portion of the ADG-comprising stream separated off at the top of the column K60 is fed to a column K80 in which ADG and organic products having a boiling point of $\geq 224.8°$ C. (1.013 bar) are separated off at the bottom and organic products having a boiling point of $\leq 224.8°$ C. (1.013 bar) are separated off at the top.

31. The process according to claim 30, wherein ADG is additionally separated off at a side offtake of the column K80.

32. The process according to claim 30, wherein products separated off at the bottom of column K80 are recirculated to the feed to the column K60.

33. The process according to claim 30, wherein products separated off at the top of column K80 are discharged or recirculated to the reaction of DEG with ammonia.

34. The process according to claim 30, wherein the column K80 has from 10 to 80 theoretical plates and is operated at a pressure of 0.005 to 3 bar.

35. The process according to claim 30, wherein the feed point of column K80 is located in the upper or middle third, based on the number of theoretical plates, and the ADG side offtake located opposite the feed point is located 1 to 30 theoretical plates below the feed point.

36. The process according to claim 1, wherein the mixture comprises morpholine, monoaminodiglycol, ammonia, water, N-ethylmorpholine, 1,2-ethylenediamine and an organic product having a boiling point of $>224.8°$ C. (1.013 bar).

37. The process according to claim 1, wherein a morpholine product is obtained having a purity of $\leq 99.5$ % by weight, an N-ethylmorpholine content of $\leq 0.20$ % by weight, a 1,2-ethylenediamine content of $\leq 0.30$ % by weight, a 2-methoxyethanol content of $<0.50$ % by weight and a water content of $\leq 0.05$ % by weight.

38. The process according to claim 1, wherein a morpholine product is obtained having an APHA color number of $\leq 10$ and a chloride content of $\leq 15$ mg/liter.

39. The process according to claim 1, wherein a morpholine product is obtained having a purity of $\geq 98.00$ % by weight, a DEG content of $\leq 0.40$ % by weight, a water content of $\leq 0.20$ % by weight and an APHA color number of $\leq 20$.

40. The process according to claim 1, wherein a morpholine product is obtained having a purity of $\geq 98.50$ % by weight, a water content of $\leq 0.30$ % by weight and an APHA color number of $\leq 50$.

41. The process according to claim 1, wherein the mixture is produced by reaction of diethylene glycol with ammonia in the presence of a heterogeneous catalyst wherein the catalyst comprises
  a) Cu, Ni or Co on a zirconium dioxide support or
  b) Cu or Ni on an aluminum oxide support.

\* \* \* \* \*